(12) United States Patent
Nikolenko

(10) Patent No.: US 8,952,708 B2
(45) Date of Patent: Feb. 10, 2015

(54) IMPEDANCE RESONANCE SENSOR FOR REAL TIME MONITORING OF DIFFERENT PROCESSES AND METHODS OF USING SAME

(71) Applicant: NeoVision LLC, Albany, CA (US)

(72) Inventor: Yury Nikolenko, San Jose, CA (US)

(73) Assignee: NeoVision LLC, Albany, CA (US)

( * ) Notice: Subject to any disclaimer, the term of this patent is extended or adjusted under 35 U.S.C. 154(b) by 133 days.

(21) Appl. No.: 13/690,859

(22) Filed: Nov. 30, 2012

(65) Prior Publication Data

US 2013/0141117 A1 Jun. 6, 2013

Related U.S. Application Data

(60) Provisional application No. 61/566,267, filed on Dec. 2, 2011.

(51) Int. Cl.
*G01R 27/28* (2006.01)
*G01R 27/26* (2006.01)
(Continued)

(52) U.S. Cl.
CPC ............. *G01N 27/028* (2013.01); *G01R 27/02* (2013.01); *G01R 27/16* (2013.01); *G01N 27/02* (2013.01); *G01R 15/12* (2013.01); *G01R 27/00* (2013.01); *G01R 27/26* (2013.01)
USPC ........... 324/655; 324/633; 324/668; 324/675; 324/708

(58) Field of Classification Search
CPC ..... G01N 27/028; G01N 27/02; G01R 27/00; G01R 27/02; G01R 27/16; G01R 27/26; G01R 15/12
USPC ......... 324/655, 654, 649, 600, 633, 629, 652, 324/668, 667, 675, 674, 681, 708, 707
See application file for complete search history.

(56) References Cited

U.S. PATENT DOCUMENTS 2,583,724 A 1/1952 Broding
3,774,103 A 11/1973 Laukien
(Continued)

FOREIGN PATENT DOCUMENTS

GB 1471480 A 4/1977
SU 1408391 A1 7/1988
(Continued)

OTHER PUBLICATIONS

Office Action for U.S. Appl. No. 12/887,887, dated Mar. 1, 2013.
Restriction Requirement for U.S. Appl. No. 12/887,887, dated Jan. 8, 2013.
Notice of Allowance and Fee(s) Due for U.S. Appl. No. 12/887,887, dated May 28, 2013.
Supplemental Notice of Allowability for U.S. Appl. No. 12/887,887, dated Jun. 20, 2013.
(Continued)

*Primary Examiner* — Hoai-An D Nguyen
(74) *Attorney, Agent, or Firm* — Pergament Gilman & Cepeda LLP

(57) ABSTRACT

Processes and apparatuses are provided for contactless measuring or monitoring in-situ and in real time composition or other electromagnetic impedance correlated properties of liquid or gaseous substances or bulk materials. One or more apparatus may include a resonance type impedance sensor having at least two coils, at least one coil of the at least two coils being at least one excitation coil connectable to at least one alternating current source with frequency sweep, at least one other coil of the at least two coils being at least one sensing coil connectable to at least one data processing system. The one or more methods may include calculating changes in amplitude and resonant frequency induced by electromagnetic interaction between said sensor and object to determine impedance of said object under test; and matching said impedance with predetermined calibration data to determine said chemical or physical properties of said object under test.

19 Claims, 11 Drawing Sheets

(51) Int. Cl.
*G01R 27/08* (2006.01)
*G01N 27/02* (2006.01)
*G01R 27/02* (2006.01)
*G01R 27/16* (2006.01)
*G01R 15/12* (2006.01)
*G01R 27/00* (2006.01)

(56) References Cited

U.S. PATENT DOCUMENTS

| | | | |
|---|---|---|---|
| 4,058,766 A | 11/1977 | Vogel et al. | |
| 4,334,604 A | 6/1982 | Davies | |
| 4,433,286 A | 2/1984 | Capots | |
| 5,003,262 A | 3/1991 | Egner et al. | |
| 5,091,704 A | 2/1992 | Kopera | |
| 5,132,617 A | 7/1992 | Leach et al. | |
| 5,213,655 A | 5/1993 | Leach et al. | |
| 5,242,524 A | 9/1993 | Leach et al. | |
| 5,343,146 A | 8/1994 | Koch et al. | |
| 5,516,399 A | 5/1996 | Balconi-Lamica et al. | |
| 5,541,510 A | 7/1996 | Danielson | |
| 5,550,478 A | 8/1996 | Kopera | |
| 5,559,428 A | 9/1996 | Li et al. | |
| 5,644,221 A | 7/1997 | Li et al. | |
| 5,659,492 A | 8/1997 | Li et al. | |
| 5,660,672 A | 8/1997 | Li et al. | |
| 5,663,637 A | 9/1997 | Li et al. | |
| 5,731,697 A | 3/1998 | Li et al. | |
| 5,770,948 A | 6/1998 | Li et al. | |
| 5,889,401 A | 3/1999 | Jourdain et al. | |
| 5,942,893 A | 8/1999 | Terpay | |
| 6,072,313 A | 6/2000 | Li et al. | |
| 6,288,507 B1 * | 9/2001 | Makino et al. | 318/293 |
| 6,310,480 B1 | 10/2001 | Cohen et al. | |
| 6,377,039 B1 | 4/2002 | Goldfine et al. | |
| 6,380,747 B1 | 4/2002 | Goldfine et al. | |
| 6,404,197 B1 | 6/2002 | Anderson et al. | |
| 6,404,199 B1 | 6/2002 | Fujita et al. | |
| 6,407,546 B1 | 6/2002 | Le et al. | |
| 6,433,541 B1 | 8/2002 | Lehman et al. | |
| 6,448,795 B1 | 9/2002 | Ermakov et al. | |
| 6,511,851 B1 | 1/2003 | Payne et al. | |
| 6,558,229 B2 | 5/2003 | Kimura et al. | |
| 6,563,308 B2 | 5/2003 | Nagano et al. | |
| 6,593,738 B2 | 7/2003 | Kesil et al. | |
| 6,602,724 B2 | 8/2003 | Redeker et al. | |
| 6,621,264 B1 | 9/2003 | Lehman et al. | |
| 6,657,433 B1 | 12/2003 | Locatelli et al. | |
| 6,663,469 B2 | 12/2003 | Kimura et al. | |
| 6,669,557 B2 | 12/2003 | Adams et al. | |
| 6,707,540 B1 | 3/2004 | Lehman et al. | |
| 6,741,076 B2 | 5/2004 | Le | |
| 6,762,604 B2 | 7/2004 | Le | |
| 6,815,947 B2 | 11/2004 | Scheiner et al. | |
| 6,878,038 B2 | 4/2005 | Johansson et al. | |
| 6,891,380 B2 | 5/2005 | Kesil et al. | |
| 6,920,399 B2 | 7/2005 | Priev et al. | |
| 6,922,065 B2 * | 7/2005 | Kawakatsu | 324/707 |
| 6,923,711 B2 | 8/2005 | Laursen et al. | |
| 6,966,816 B2 | 11/2005 | Swedek et al. | |
| 6,975,107 B2 | 12/2005 | Hanawa et al. | |
| 6,977,503 B2 | 12/2005 | Prado | |
| 7,008,296 B2 | 3/2006 | Swedek et al. | |
| 7,008,297 B2 | 3/2006 | Johansson et al. | |
| 7,016,795 B2 | 3/2006 | Swedek et al. | |
| 7,043,402 B2 | 5/2006 | Phillips et al. | |
| 7,046,001 B2 | 5/2006 | Tada et al. | |
| 7,070,476 B2 | 7/2006 | Lehman et al. | |
| 7,074,109 B1 | 7/2006 | Bennett et al. | |
| 7,078,894 B2 | 7/2006 | Tada et al. | |
| 7,095,230 B2 | 8/2006 | Blumich et al. | |
| 7,135,870 B2 | 11/2006 | Mohajer et al. | |
| 7,195,536 B2 | 3/2007 | Swedek et al. | |
| 7,198,545 B1 | 4/2007 | Korovin et al. | |
| 7,219,024 B2 | 5/2007 | Gamache et al. | |
| 7,247,080 B1 | 7/2007 | Bennett et al. | |
| 7,332,902 B1 | 2/2008 | Vermeire et al. | |
| 7,352,186 B2 | 4/2008 | Hasegawa et al. | |
| 7,374,477 B2 | 5/2008 | Birang et al. | |
| 7,500,901 B2 | 3/2009 | Swedek et al. | |
| 7,508,201 B2 | 3/2009 | Tada et al. | |
| 7,514,938 B2 | 4/2009 | Publicover et al. | |
| 7,591,708 B2 | 9/2009 | Birang et al. | |
| 7,619,414 B2 | 11/2009 | Yamamoto et al. | |
| 7,635,331 B2 | 12/2009 | Kim et al. | |
| 7,659,731 B2 | 2/2010 | Lin et al. | |
| 7,682,221 B2 | 3/2010 | Swedek et al. | |
| 7,714,572 B2 | 5/2010 | Tada et al. | |
| 7,737,038 B2 | 6/2010 | Lee et al. | |
| 7,795,866 B2 | 9/2010 | Fujita | |
| 7,822,500 B2 | 10/2010 | Kobayashi et al. | |
| 7,836,756 B2 | 11/2010 | Boudaoud et al. | |
| 7,912,661 B2 | 3/2011 | Zeng et al. | |
| 8,106,657 B2 | 1/2012 | Sakellariou et al. | |
| 8,547,110 B2 | 10/2013 | Kesil et al. | |
| 2003/0181827 A1 | 9/2003 | Hojeibane et al. | |
| 2005/0156604 A1 | 7/2005 | Red'ko et al. | |
| 2007/0103150 A1 | 5/2007 | Tada et al. | |
| 2008/0143345 A1 | 6/2008 | Boudaoud et al. | |
| 2008/0199359 A1 | 8/2008 | Davis et al. | |
| 2009/0027070 A1 | 1/2009 | Gelling | |
| 2009/0061733 A1 | 3/2009 | Fujita et al. | |
| 2009/0079424 A1 | 3/2009 | Tralshawala et al. | |
| 2009/0128272 A1 | 5/2009 | Hills | |
| 2009/0132174 A1 | 5/2009 | Burke et al. | |
| 2010/0253371 A1 | 10/2010 | Bierl et al. | |
| 2010/0327884 A1 | 12/2010 | McCall et al. | |
| 2011/0068807 A1 | 3/2011 | Kesil et al. | |
| 2012/0187905 A1 * | 7/2012 | Kanayama | 320/109 |
| 2012/0293188 A1 * | 11/2012 | Nikolenko et al. | 324/655 |
| 2013/0141095 A1 | 6/2013 | Nikolenko | |

FOREIGN PATENT DOCUMENTS

| | | |
|---|---|---|
| WO | 2008076453 A1 | 6/2008 |
| WO | 2008145188 A1 | 12/2008 |
| WO | 2011038003 A1 | 3/2011 |

OTHER PUBLICATIONS

Supplemental Notice of Allowability for U.S. Appl. No. 12/887,887, dated Jun. 25, 2013.
Response to After Allowance Amendment for U.S. Appl. No. 12/887,887, dated Jul. 26, 2013.
Notification of Transmittal of the International Preliminary Report on Patentability, dated Nov. 19, 2013, for International Pat. App. No. PCT/US2012/038369, notification mailed on Nov. 28, 2013.
International Preliminary Report on Patentability for International Pat. App. No. PCT/US2012/038369 and attached Written Opinion of the International Searching Authority for International Pat. App. No. PCT/US2012/038369, report dated Nov. 19, 2013.
International Search Report and Written Opinion for PCT/US2010/049824, dated Feb. 10, 2011.
B. Jeanneret, J. L. Gavilano, G. A. Racince, CH. Leemann and P. Martinoli: "Inductive conductance measurements in two-dimensional superconducting systems", Applied Physics Letters, vol, 55, No. 22, pp. 2336-2338, dated Nov. 27, 1989.
Notification Concerning Transmittal of International Preliminary Report on Patentability—Chapter I of the Patent Cooperation Treaty, dated Apr. 5, 2012, for International Pat. App. No. PCT/US2010/049824.
International Preliminary Report on Patentability, dated Mar. 27, 2012.
Written Opinion of the International Searching Authority for International Pat App. No. PCT/2010/049824.
Notification of Transmittal of the International Search Report and Written Opinion for PCT/US2012/038369, dated Nov. 6, 2012.
The International Search Report for PCT/US2012/038369.
Written Opinion for PCT/US2012/038369.

* cited by examiner

IMPEDANCE RESONANCE SENSOR FOR REAL TIME MONITORING OF DIFFERENT PROCESSES AND METHODS OF USING SAME

CROSS-REFERENCE TO RELATED APPLICATION(S)

This application is a non-provisional patent application that claims the benefit of the filing date of, and priority to, pending U.S. provisional patent application No. 61/566,267, filed Dec. 2, 2011, the entirety of which is incorporated herein by reference.

BACKGROUND OF THE INVENTION

The present invention relates in general to one or more methods and apparatuses for determining selected properties and various constituents concentration in liquids, gaseous and solid solutions as well as determining other properties such as density and moisture content of many varieties of solid and gaseous materials. More particularly, the present invention relates to one or more methods and apparatuses for determining concentration of individual components within a mixture by utilizing method of Electrochemical Impedance Spectroscopy which measures the electric properties of a medium as a function of frequency.

Determination of mixture composition is a commonly encountered need. It is no wonder that huge amount of inventions are dedicated to this important task. One of possible means is to analyze electrical properties of target mixture. Most commonly means for determining mixture composition are contact electrode methods. Unfortunately, prior devices are deficient for a plurality of reasons, including, but not limited to, the fact that one or more sensors of such prior devices lack the desired sensitivity, the one or more sensors must be located in inconvenient location(s) with respect to the composition/object being evaluated or tested, etc. As such, there is a need in the art to create an improved invention with enhanced sensitivity for determining one or more mixture compositions or for otherwise obtaining data from an object under test.

It would also be desirable to provide an invention that permits the ideal location of the sensors and/or other components thereof with respect to the composition and/or the object under test.

SUMMARY OF THE INVENTION

The invention relates to electrical devices and, more particularly, to a highly sensitive impedance resonant (IR) sensor with a sensing head, which is an open-core or air core sensing inductor with excitation and sensing coils.

Several improvements of Impedance Resonance (IR) sensor apparatuses and methods of use are disclosed. One or more aspects of the present invention also may be employed in conjunction with a suitable IR sensor, including, but not limited to, the IR sensor of co-pending U.S. patent application Ser. No. 12/887,887, Filing Date: Sep. 22, 2010, the entirety of which is incorporated herein by reference. These improvements of the present invention supplement basic variant with additional advanced merits and attributes. Two disclosed modifications or improvements bear a relation to one or more methods for acquiring results of measurement made by at least one sensor. Other modification(s) or improvement(s) enhance sensitivity of the at least one sensor by exploiting change of a sensing coil distributing capacitance (turn-to-turn capacitance) while immersing the sensing coil into, adjacent to, or near at least one liquid, gaseous or bulk material object under test. Another modification or improvement relates to the location of the one or more sensing and excitation coils. This additional or alternative modification or improvement unveils the possibility of placing the sensing coil into a vessel whereas the excitation coil encompasses the vessel.

In accordance with one or more purposes and/or aspects of the present invention, as embodied and/or broadly described herein, one or more embodiments of the present invention may use both modified and basic variants of the IR sensor. At least one embodiment may use the IR sensor with an immersible sensing coil for evaluating properties of a liquid, such as, but not limited to, an oil, motor oil, milk, chlorine concentration in water, moisture in soil, dextrose concentration in saline, etc. At least one embodiment of the invention may determine the presence of one or more selected, or predetermined, elements in one or more lubrication oils by means of an electromagnetic field probing same based on resonance impedance technology, and may alert an end-user of the device when a concentration of at least one of the preselected harmful constituents measured by one of the IR sensors exceeds an allowable, or a predetermined, concentration level. At least an additional embodiment of the invention may be dedicated to measuring the concentration of one or more milk ingredients. At least a further embodiment of the invention may be used to measure soil moisture. Yet a further embodiment of the invention may operate to measure a dextrose concentration in saline. Still, yet another embodiment of the invention may be dedicated to the measurement of a residual chlorine concentration in tap water.

An apparatus, method for monitoring without contact in situ and real time of selected properties and various constituents concentration in liquids, gaseous and solid solutions as well as determining other properties such as density and moisture content of many varieties of solid and gaseous materials, are disclosed. The invention also includes an Impedance Resonance (IR) sensor model for use for selected samples with the above-described aspects. In one embodiment, the invention determines presence of selected elements in lubrication oils based on an effect of resonance impedance characteristics of the solution on an electromagnetic field, and alerts an end-user when concentration of one of the preselected harmful constituents by one of the IR sensors exceeds allowable concentration levels. Change of the conductivity and dielectric properties of the solution will change the impedance of the IR sensor's excitation or sensing coil. The harmful constituent's concentration indication is determined based on one or more solution properties, temperature and quantity of the solution.

The invention relates to electrical devices and, more particularly, to a highly sensitive impedance resonant (IR) sensor with a sensing head, which is an open-core or air core sensing inductor with excitation and sensing coils.

Additionally or alternatively, a resonance type impedance sensor, which is a multicoil open-core or air-core inductor, may include at least two coils, at least one coil of the at least two coils being at least one excitation coil connectable to at least one alternating current source with frequency sweep, at least one other coil of the at least two coils being at least one sensing coil connectable to at least one data processing system, wherein: (i) upon electrical connection to said current source, said at least one excitation coil is capable of propagating an energy to said at least one sensing coil, which is capable of generating a probing electromagnetic field, (ii) said at least one sensing coil is designed in such a way that intrinsic inductance L, capacitance C, and resistance R parameters of said at least one sensing coil are capable of providing resonance conditions for measuring of object under test impedance at predetermined frequency, said object under test capable of being at least one of conductive, semi-conductive and non-conductive, and (iii) said at least one sensing coil is not connected to a capacitance means located externally to said at least one sensing coil such that said at least one sensing coil is capable of measuring at least one of conductance and one or more dielectric properties of at least a part of said object under test falling within a sensing area or range of said at least one sensing coil.

BRIEF DESCRIPTION OF THE DRAWINGS

For purposes of illustrating the various aspects of the invention, wherein like numerals indicate like elements, there are shown in the drawings simplified forms that may be employed, it being understood, however, that the invention is not limited by or to the precise arrangements and instrumentalities shown. To assist those of ordinary skill in the relevant art in making and using the subject matter hereof, reference is made to the appended drawings and figures, wherein.

DETAILED DESCRIPTION

Figure 1:
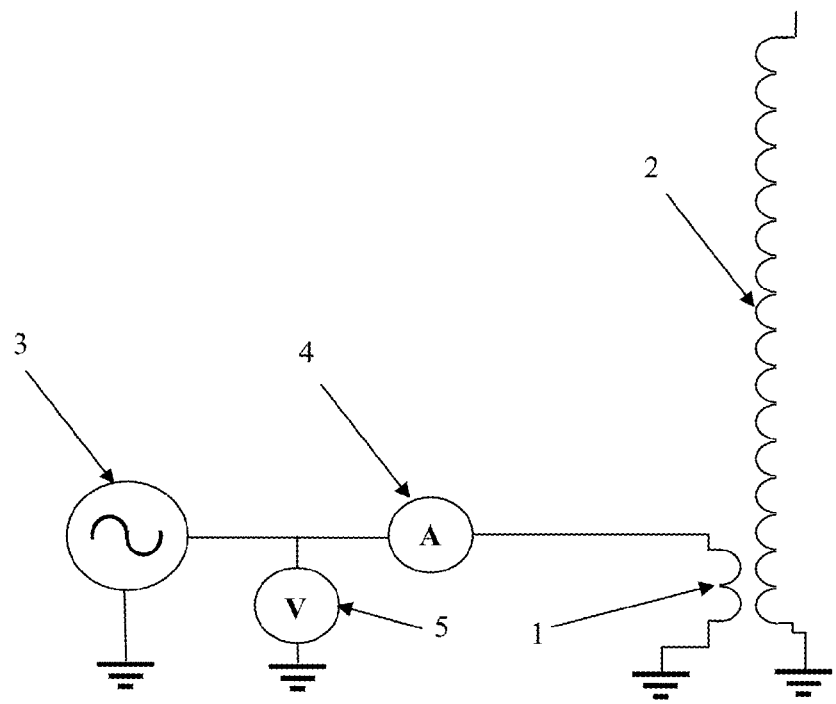
FIG. 1 is a schematic of an electrical circuit of one embodiment of a sensor to illustrate a method of acquiring a signal from the sensing head of an IR Sensor with Open-Circuit Sensing Coil in accordance with one or more aspects of the present invention.

1 Structure and Principle of Operation of at Least One Embodiment of an IR Sensor with an Open-Circuit Sensing Coil 1.1 Modification/Improvement in which Information is Obtained from Excitation Coil A schematic electrical circuit of one embodiment of a sensor of the present invention is shown in FIG. 1. Similar to the sensor disclosed in our U.S. patent application Ser. No. 12/887,887, the entirety of which is incorporated herein by reference, the sensor of the present invention comprises a two-coil inductor with an open or air core. One coil, i.e., a coil 1, is an excitation coil, and the second coil, i.e., a coil 2, is a sensing or measurement coil.

At least one embodiment of the sensor operates as follows: A frequency-based sweep generator 3, which functions as the source of a variable-frequency electric field, feeds the excitation coil 1. The frequency variation range of the generator includes resonance frequency of the sensing coil 2. Being in an electromagnetic coupling with the sensing coil 2, the excitation coil 1 brings the latter into a state of self-resonance. The condition of self-resonance leads to a significant increase in the intensity of the electromagnetic field induced by the inductor, e.g., by its sensing coil. A test object placed into this electromagnetic field develops eddy currents and/or vortex displacement currents, which, in turn, generate their own electromagnetic fields that are perceived by the sensing coil. Such interaction changes not only the resonance frequency but also the amount of dissipated electromagnetic energy. In order to compensate for this loss of energy, the current in the circuit comprising the frequency-based sweep generator 3 and the excitation coil automatically increases. This process is similar to transfer of a transformer from the idle mode to the under-load mode of operation. Such variation in flow of electromagnetic energy can be registered by a high-frequency ammeter 4 and a voltmeter 5, but the use of only an ammeter is sufficient.

Figure 2:
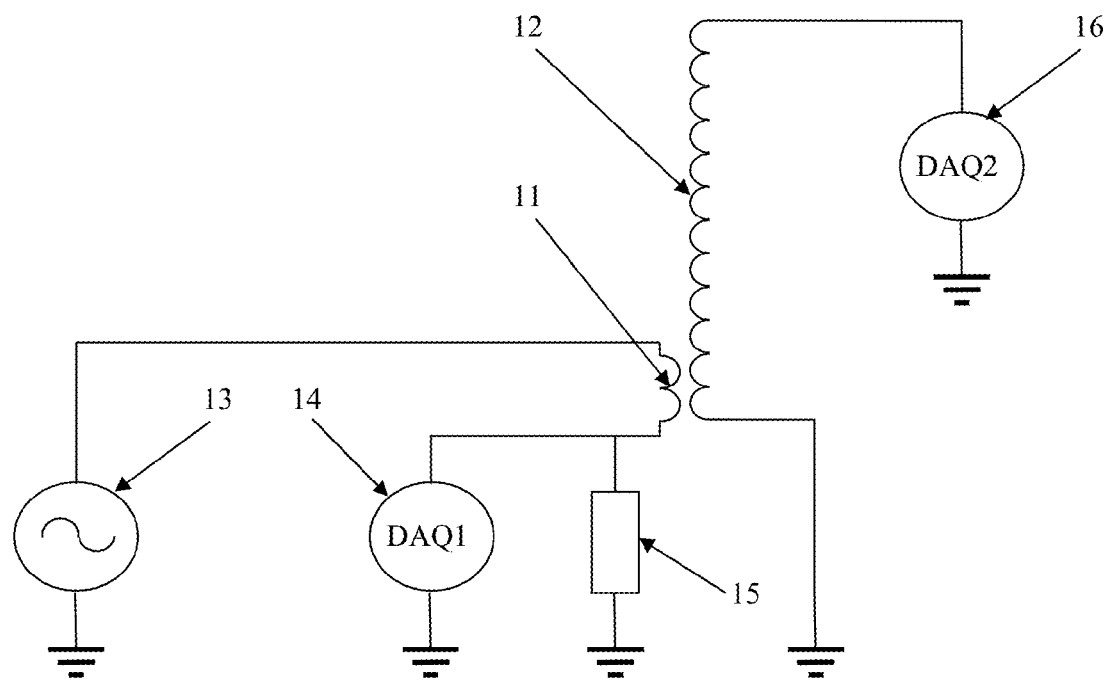
FIG. 2 is a schematic of an electrical circuit of another embodiment of a sensor to illustrate a method of acquiring a signal from the sensing head of an IR sensor, wherein information is obtained from both the sensing coil and the excitation coil, in accordance with one or more aspects of the present invention.

1.2 Modification/Improvement in which Information is Obtained from at Least One Sensing Coil and at Least One Excitation Coil FIG. 2 shows at least one embodiment of a sensor including a modification wherein information is obtained from both the sensing coil and the excitation coil of the sensor. Similar to the sensor shown in FIG. 1, the sensor of the present embodiment of FIG. 2 is a two-coil inductor with an open or air core. One coil is an excitation coil 11, and the second coil is a sensing or measurement coil 12. A distinguishing feature of the sensor of this embodiment is formation of the signal, which corresponds to impedance characteristics of a test object, with use not only of a sensing coil circuit (components 12 and 16) but also with participation of the excitation coil (components 11, 13, 14 and 15).

As explained above, impedance of the test object affects electrical parameters not only in the sensing circuit, which is in the state of resonance, but also in the excitation circuit. The current that flows through the excitation coil grows proportionally with the amount of electromagnetic energy dissipated from the test object. Such change in the current increases voltage amplitude on a bypass resistor 15, and a data acquisition unit 14 registers the voltage increase.

Electrical characteristics of the sensing circuit of the highly sensitive IR sensor of the invention change in the same or similar manner as described in the aforementioned pending U.S. patent application Ser. No. 12/887,887. Interaction of the sensor with the test object changes resonance frequency and resonance amplitude, which are registered by a data acquisition unit 16.

A useful measurement signal may be formed by using various combinations of data obtained by the data acquisition units 14 and 16. For example, the following data can be used:
(a) signal difference: "$V_m - V_{ex}$" or "$V_{ex} - V_m$" (where $V_m$ is measurement voltage and $V_{ex}$ is excitation voltage); and/or
(b) signal ratio: "$V_m/V_{ex}$" or "$V_{ex}/V_m$".

For example, in at least one embodiment of a CMP (Chemical Mechanical Polishing) sensor developed by the applicant on the basis of the present invention, a useful signal (data obtained from the sensor) is formed by using an RF/IF (radio frequency/intermediate frequency) Gain and Phase Detector, which comprises a dual-channel demodulating logarithmic amplifier with a phase detector. Characteristics of this instrument are as follows: operating frequency range of about 0 to about 2.7 GHz; minimal output signal of about 30 mV, which corresponds to $-20 \times \text{Log}(V_{ex}/V_m) = -30$ dB; and maximal output signal of about 1.8V, which corresponds to $-20 \times \text{Log}(V_{ex}/V_m) = +30$ dB.

Resonance frequency can be determined by means of:
a) frequency sweeping and searching of the maximum (or minimum) value of the useful signal; or
b) using information obtained from a phase detector (this method is based on one of the fundamental conditions of resonance, i.e., the absence of a phase shift between forced oscillations that are induced by the excitation circuit and natural electromagnetic oscillations of the sensing coil).

Figure 3:
FIG. 3 illustrates a design of a cylindrical sensing coil that uses turn-to-turn capacitance to improve sensitivity of the IR sensor in accordance with one or more aspects of the present invention.

1.3 Modification/Improvement of a Sensing Coil Included in the Structure of One or More IR Sensors of the Invention with Sensitivity Improved Based on an Effect of the Dependence of Turn-to-Turn Capacitance from Dielectric Properties of Liquid, Powdered, or Gaseous Test Object(s) that Fill(s) a Space Between Turns and Layers of the Aforementioned Sensing Coil In our pending U.S. patent application Ser. No. 12/887,887, the entirety of which is incorporated herein by reference, we focused on the fact that in order to improve sensitivity of the IR sensor to dielectric properties of the test object, it is useful to minimize natural capacitance of the sensing circuit. The sensing circuit of aforementioned sensor comprises the sensing coil only, and turn-to-turn capacitance of the sensing coil is considered as a "parasitic" one. The demand for minimization of turn-to-turn capacitance is absolutely justifiable for all the examples used in the aforementioned patent application. In examples of that patent application, a substance that fills the space between the turns and layers of the sensing coil before beginning the measurement process remains the same during the measurement process. For a sensor of this application (e.g., where the sensing coil is immersed into a test object), measurement conditions are quite different since in this case the useful signal includes changes caused in the turn-to-turn and in the interlayer capacitance of the sensing coil by the material of the test object that fills the spaces between the turns of the coil. In order to enhance this effect, a coil with a rectangular rather than a circular cross-section is preferably used, as shown in FIG. 3. In this case, the surface area of the so-called "turn-to-turn" capacitance is considerably increased.

Figure 4:
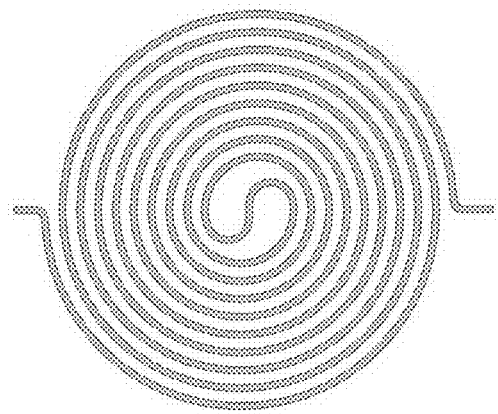
FIG. 4 illustrates a design of a flat sensing coil that uses turn-to-turn capacitance to improve sensitivity of the IR sensor in accordance with one or more aspects of the present invention.
Figure 5:
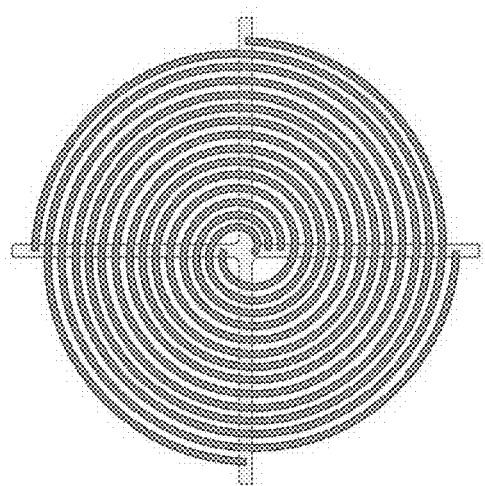
FIG. 5 illustrates a design of a multi-entry flat sensing coil that uses turn-to-turn capacitance to improve sensitivity of the IR sensor in accordance with one or more aspects of the present invention.

FIG. 4 and FIG. 5 illustrate other design embodiments of sensing coils that use turn-to-turn capacitance to improve sensitivity of the IR sensor.

An excitation coil may have different positions relative to a sensing coil:
a) in a cylindrically shaped sensing coil (FIG. 3), the excitation coil may be arranged at the end face (left or right) of the sensing coil or may embrace the sensing coil in any location, as described below in Section 1.4;
b) in a flatly shaped sensing coil (FIG. 4 and FIG. 5), the excitation coil may surround the sensing coil being in the same plane therewith; alternatively, the excitation coil may be located on either side and in proximity to the sensing coil in a plane parallel with the latter; and/or
c) the excitation coil may be arranged as described below in Section 1.4.

Any of the three methods (two of which are described above in Sections 1 and 2 and one in our aforementioned patent application Ser. No. 12/887,887, which is incorporated herein by reference in its entirety) can be used to obtain information from the IR sensor of the invention.

In Section 2.1 an example of one or more possible applications for these kinds of sensors is discussed below, and given measurements results therefor correspond to, and indicate, degradation of motor oil.

1.4 Modification/Improvement of at Least One IR Sensor of the Present Invention Wherein at Least One Sensing Coil is Immersed into or Near a Test Object Material Located in a Tube (or Vessel) and with an Excitation Coil Located Outside the Tube (or Vessel)

Figure 6:
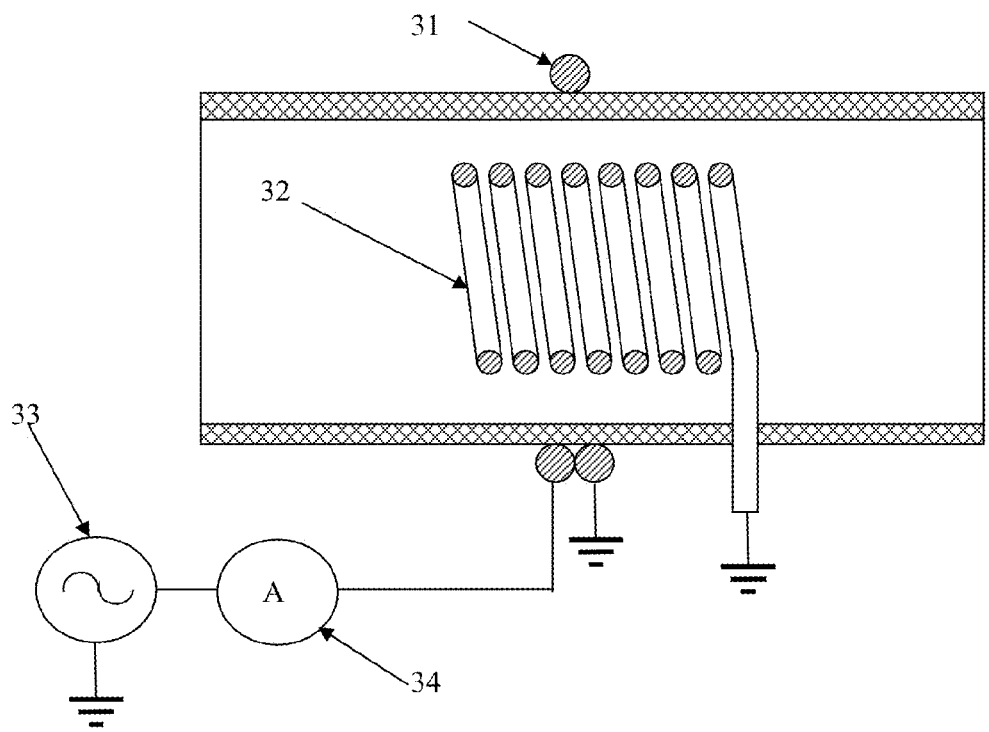
FIG. 6 illustrates a design of an immersible sensing coil separated from an excitation coil in accordance with one or more aspects of the present invention.

In at least one embodiment, the sensing coil 32 is located inside a tube or vessel, while the excitation coil 31 is located outside the tube or the vessel (FIG. 6). This structure is based on the principle of an IR sensor with the open-loop type of sensing coil described in Section 1 of this specification. The frequency-based sweep generator 33 comprises a variable-frequency source. Preferably, the resonance frequency of the sensing coil 32 is included in the frequency variation range. Measurement data are obtained from a high-frequency ammeter 34.

2 EXAMPLES

While not intended to be an exhaustive list of the structural arrangements of, or ways to use, one or more IR Sensors of the present invention, several embodiments of one or more IR Sensors are disclosed herein to illustrate how the one or more IR Sensors may be used to evaluate one or more properties of various types of object(s) under test (whether liquid, solid, gaseous or otherwise), such as, but not limited to, oil, motor oil, milk, chlorine in water, slurry, etc.

2.1 Example 1

Use of an IR Sensor to Evaluate Properties of Motor Oil

Description of experiment:
1. Three samples of motor oil were obtained from auto repair shop:
   fresh new oil;
   motor oil after 3678 miles of usage; and
   motor oil after 7801 miles of usage.
2. The samples were placed in three vials of 15 cc volume.
3. An IR sensor having a sensing coil of the type shown in FIG. 3 has been immersed in each of the vials by turns.

Figure 7:
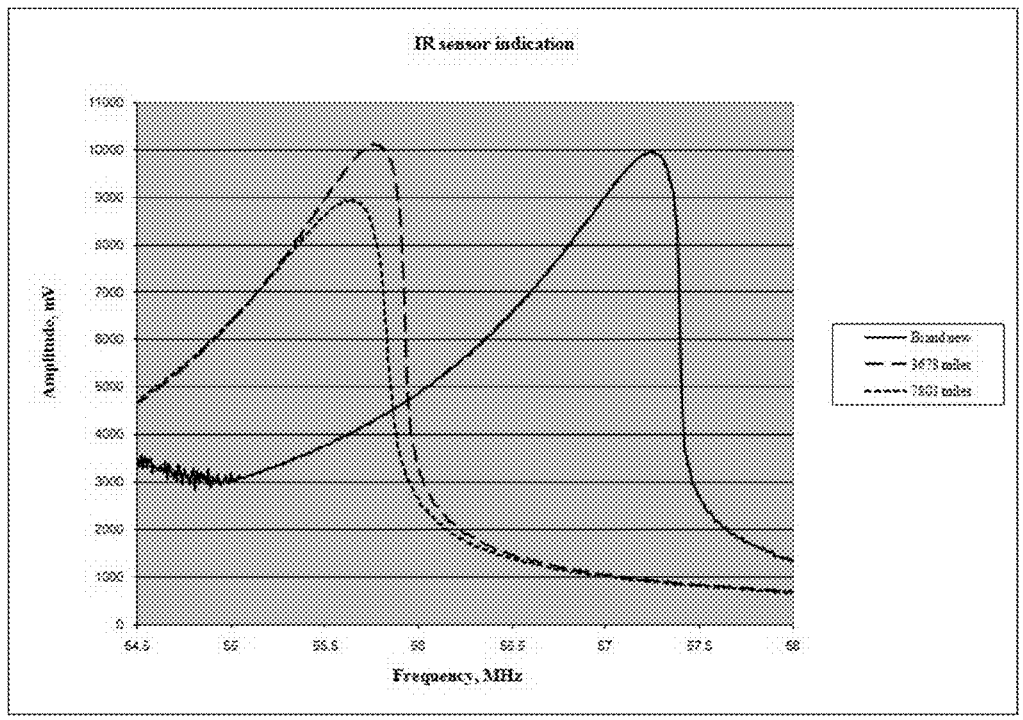
FIG. 7 depicts an IR sensor's Gain-Frequency Variations for different motor oil samples in accordance with one or more aspects of the present invention.
Figure 8:
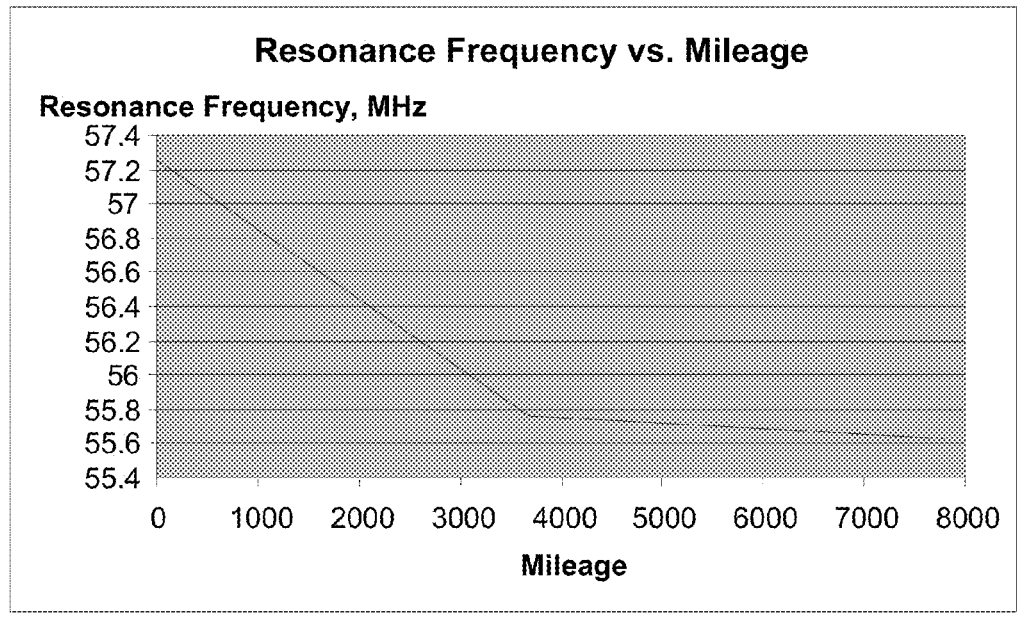
FIG. 8 depicts changing of an IR sensor's resonance frequency relatively changing of motor oil mileage in accordance with one or more aspects of the present invention.
Figure 9:
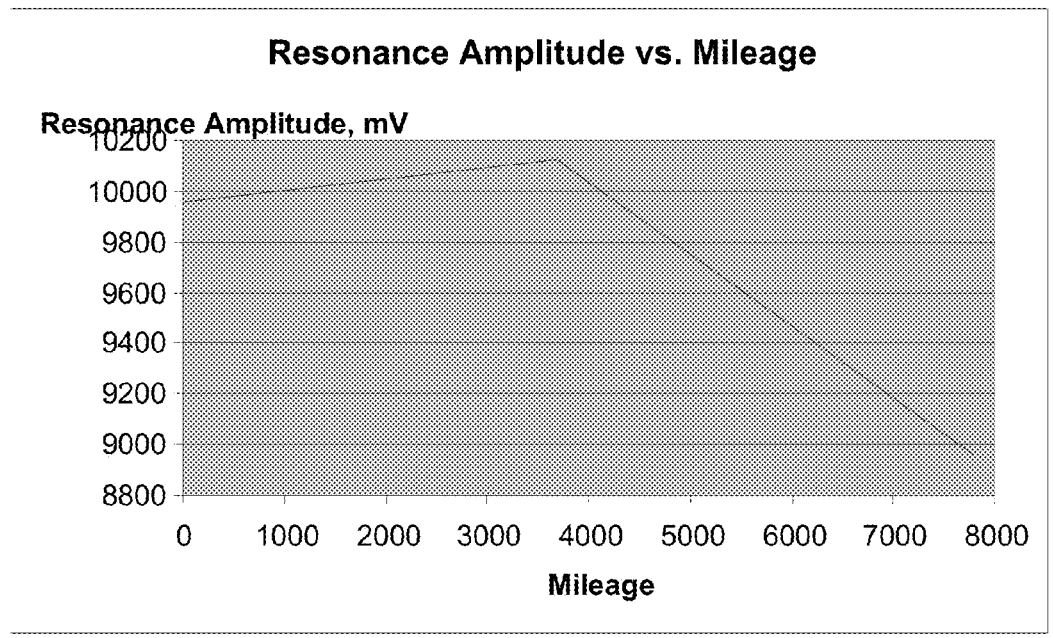
FIG. 9 depicts changing of an IR sensor's resonance amplitude relatively changing of motor oil mileage in accordance with one or more aspects of the present invention.

Results of the measurement are shown in FIG. 7, FIG. 8, and FIG. 9.

2.2 Example 2

Use of at Least One System of IR Sensors for Real Time Monitoring of a Quality of Slurry During a CMP Process At least one embodiment of the invention is directed to real time monitoring quality of slurry during a CMP process. It is critical to reduce wafer defects during the polishing process and lower cost of ownership in current and next generation CMP tools. To maintain CMP slurry health during usage, it is essential to monitor and control slurry's chemical (e.g., oxidizer and additive levels and their decay behavior), as well as abrasive properties, including particles size distribution (PSD), large particle counts (LPC), density, etc. The method allows in real time monitoring of the oxidizer concentration as well as the abrasive particle information in CMP slurry blends. This works on the principles of chemometrics, which is a two-phase process. In the first "calibration" phase, samples with known property values are measured by the system. A mathematical procedure then determines the correlation between the measured spectra and true property values. The output of this phase is a "model" that optimally calculates the parameter values from the measured spectra of the calibration samples. In the second "measurement" phase, unknown samples are measured by the system employing the model to produce estimates of the property values.

The system may comprise of various types of IR sensors designed for measurement of liquids. The system may include one or more sensors that have no contact with the slurry as described in U.S. patent application Ser. No. 12/887,887, sensors as described in U.S. provisional patent application No. 61/566,267, such as in paragraph 1.3 thereof, as described herein, etc.

2.3 Example 3

Figure 10:
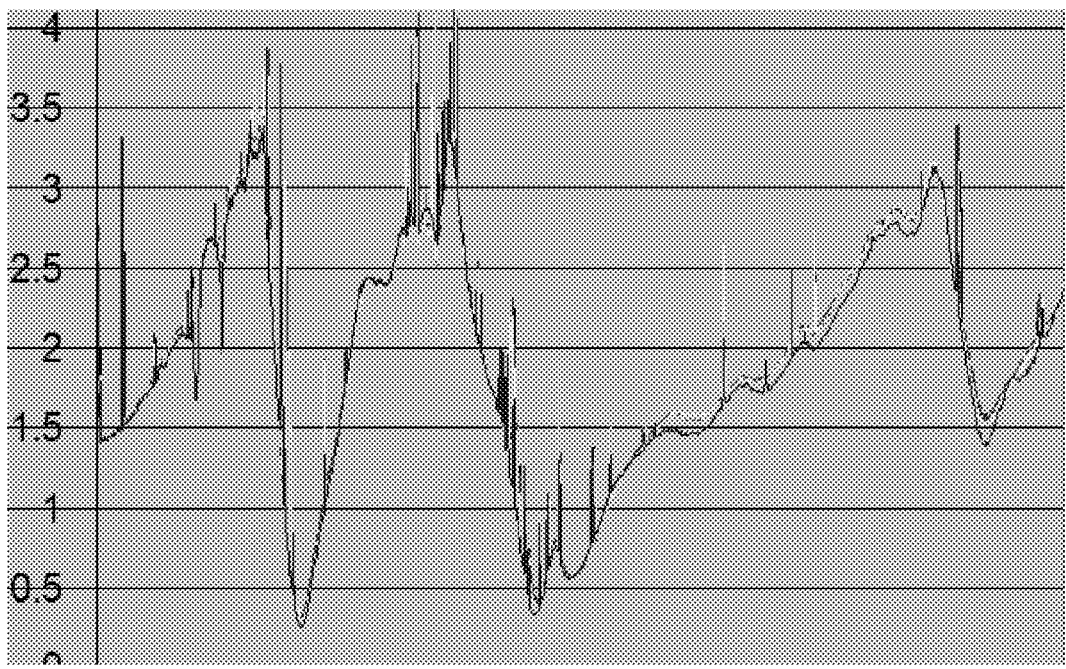
FIG. 10 depicts a graph of scans for different milk samples using a potentiostate in accordance with one or more aspects of the present invention.

IR Measuring of Somatic Cell Count, Lactose Concentration and Fat Content in Milk Using a standard potentiostat we identified areas where an electrical field influences various milk components. FIG. 10 shows a "screen shot" or graph of five different milk samples scanned with a potentiostate in a frequency range from about 10-about 170 MHz. We can see on the screen shot/graph areas where graph plots for different milk samples split in amplitude. These are areas where phenomena of impedance spectroscopy take place. In those areas, influence of each individual constituent can be defined. These scans show a large number of possible frequencies that could be used for measurement of milk components.

In order to identify the best fitted frequencies, we used three milk samples with the minimum and maximum concentrations of target constituent: 1) skim milk (about 0% fat) and 3.2% pasteurized milk to identify the frequency of monitoring fat content; 2) pasteurized 3.2% fat milk and farm milk with fat about 3.2% but with great difference in Somatic Cell Count (SCC) to define the frequency where SCC has the strongest response; and 3) 3.2% pasteurized milk with lactose free milk and the second sample with lactose and about the same fat content (3.2%) to define the frequency where lactose has the strongest response.

Figure 11:
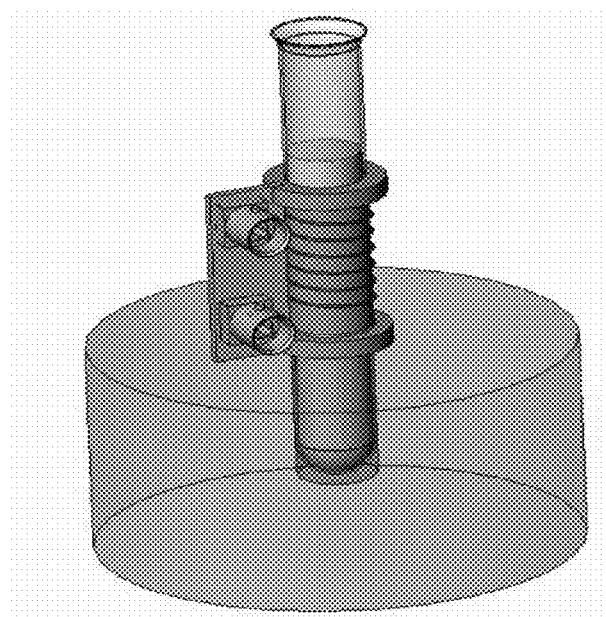
FIG. 11 depicts a schematic design of an IR sensor for measurement of liquid in accordance with one or more aspects of the present invention.

Using data from the potentiostate we defined that at frequency of about ~126 MHz we got sufficient sensitivity for measuring SCC, at frequency of about ~117 MHz to lactose, and at frequency of about ~131 MHz to milk fat. Those data permitted us to calculate measuring circuits' parameters at frequencies close to those identified. We constructed measuring circuits (coils) and mounted them on a fixture (FIG. 11). We placed milk specimens with known characteristics in vials and recorded signal gain-frequency variations.

Figure 12:
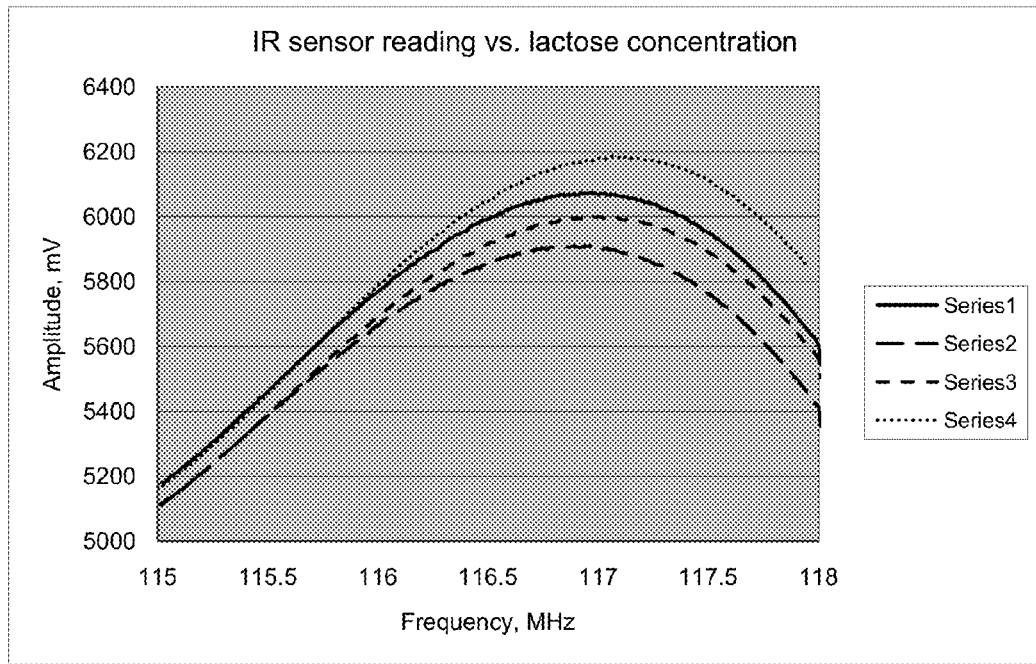
FIG. 12 depicts a graph of amplitude versus lactose concentration in samples of milk analyzed using IR sensors in accordance with one or more aspects of the present invention.
Figure 13:
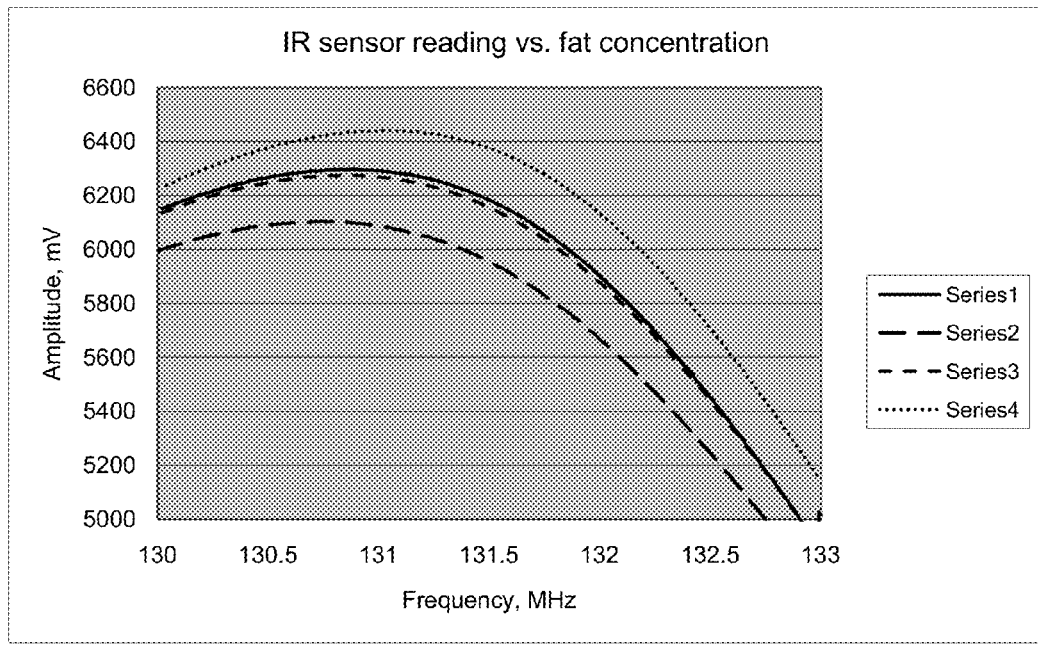
FIG. 13 depicts a graph of amplitude versus fat concentration in samples of milk analyzed using IR sensors in accordance with one or more aspects of the present invention.
Figure 14:
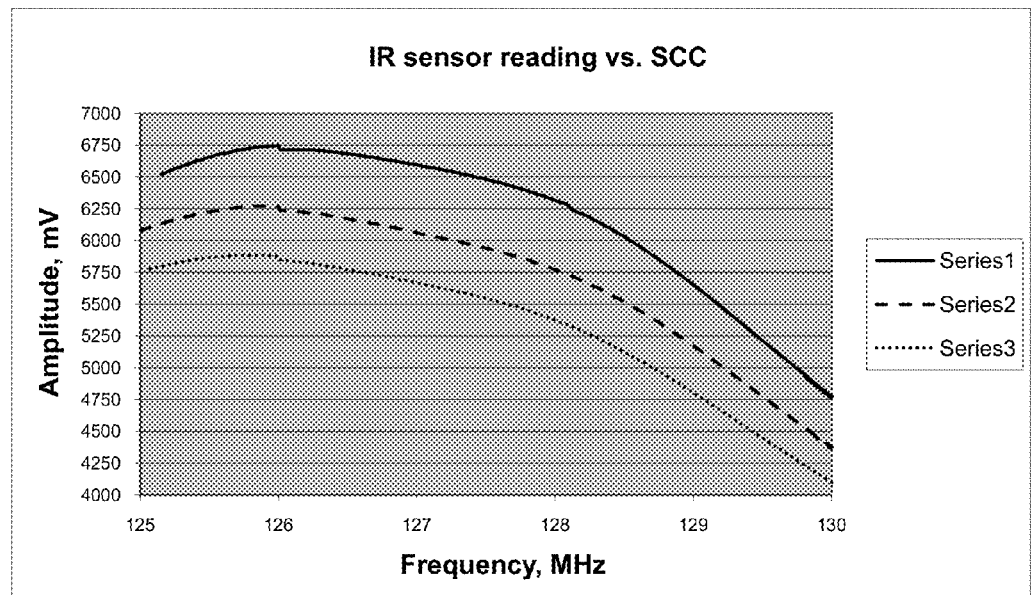
FIG. 14 depicts a graph of IR amplitude changing versus frequency for solutions containing different somatic cell counts ("SCC") analyzed using IR sensors in accordance with one or more aspects of the present invention.
Figure 15:
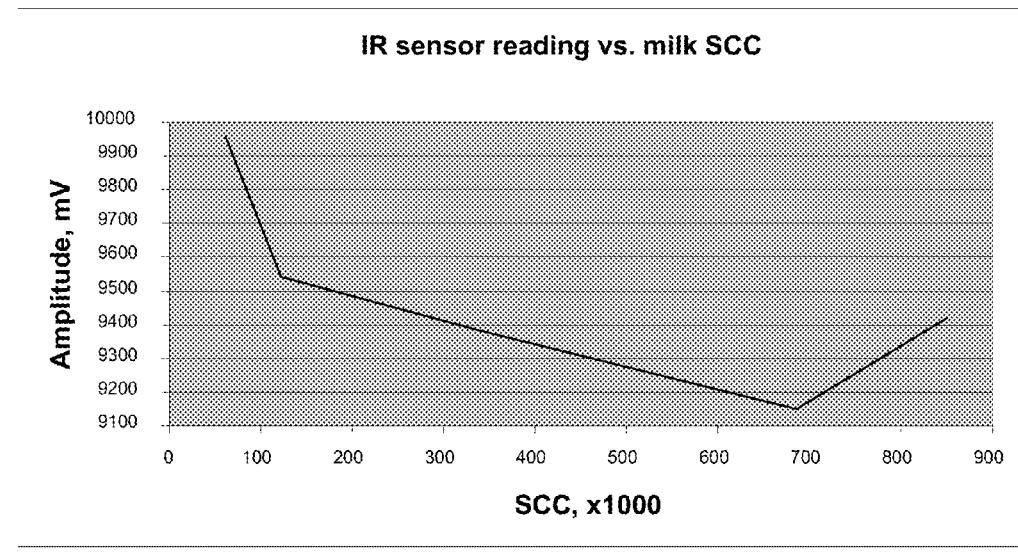
FIG. 15 depicts a graph of IR resonance amplitude changing versus SCC for samples of milk analyzed using IR sensors in accordance with one or more aspects of the present invention.

In our experiments, the concentration of lactose was changed by dilution of whole milk with lactose free milk, and the concentration of milk fat was changed by dilution of 3.2% milk with skim milk. In the experiments shown in series 1, no lactose or fat were present in the milk samples. Contrary, the experiments in series 4 scans showed maximum content of lactose (FIG. 12) and fat in milk (FIG. 13). Series 2 and 3 correctly showed increasing levels of lactose and fat in milk samples. Experiments with measuring lactose and fat were made with samples where known concentrations were diluted. All experiments related to SCC were confirmed experimentally by DCC (DeLaval Cell Counter), scans of SCC shown on FIG. 14. We used just one kind of milk and added to it cells to change SCC concentration. The signal reading correlated with SCC at fixed frequency is not monotonic (FIG. 15).

Figure 16:
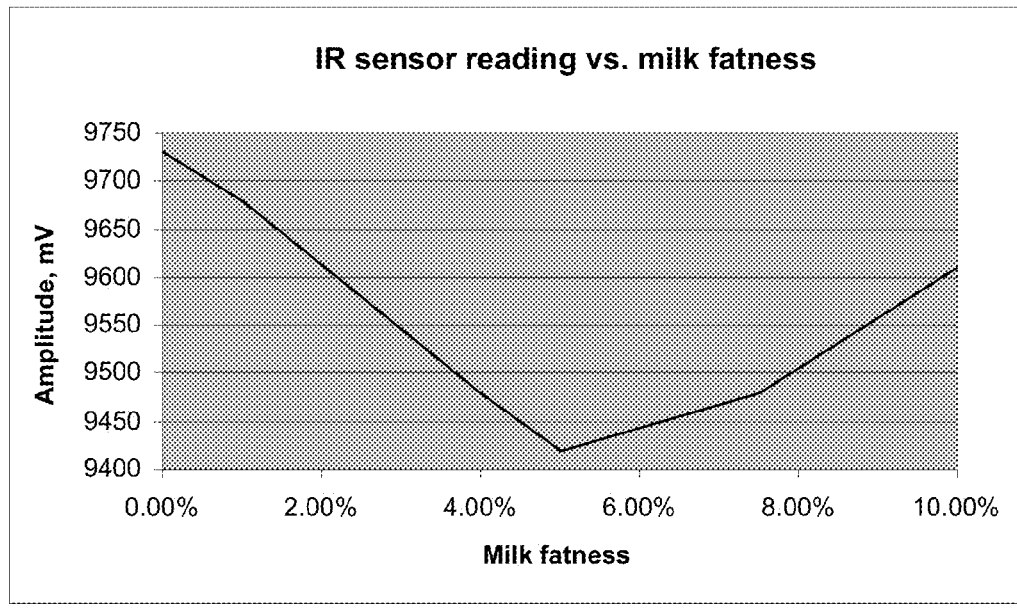
FIG. 16 depicts a graph of IR resonance amplitude versus fat content in samples of milk analyzed using sensors in accordance with one or more aspects of the present invention.

The process of measuring fat content in milk is similar to measuring SCC (FIG. 15) that was described above. The signal reading correlated with milk fat at fixed frequency is in FIG. 16. FIG. 15 and FIG. 16 show non-monotonic constituents' response to IR probing and measuring of those constituents. Preferably, such probing and/or measuring is done with two sensors per each constituent. The experiments with milk show the possibility to monitor each of the constituents' concentration in their natural range of fluctuation in very complex structures.

Figure 17:
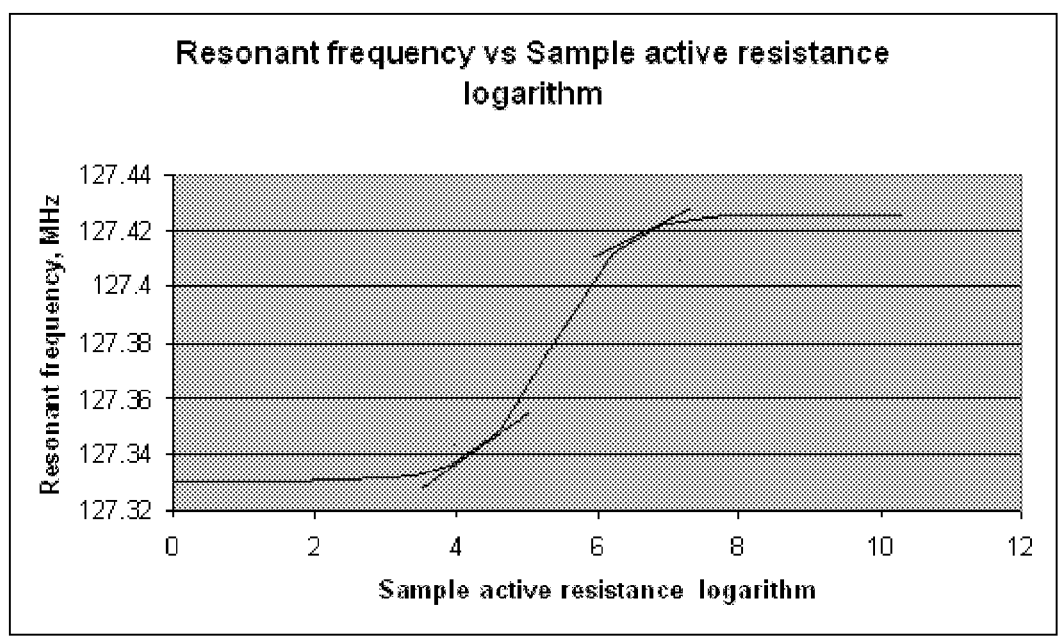
FIG. 17 depicts a graph of resonant frequency versus the logarithm of active resistance in a series of samples analyzed using IR sensors in accordance with one or more aspects of the present invention.

The mathematical simulation of constituents measuring where probing with IR yields non-monotonic graphs help to define two frequencies for building sensors. FIG. 17 is a graph depicting the two results of 127.34 MHz and 127.42 MHz. These frequencies are data for constructing measuring coils for SCC.

Thus, we have identified new problems in the analytic arts, and have provided new solutions for these as well as for known problems in the art. Using a multiple-sensor system of this invention, it is now possible to measure multiple different constituents simultaneously, in real-time, and without increasing risks associated with either removing samples from a stream of production or from contaminating the stream with unwanted materials introduced during sampling.

2.4 Example 4

IR Measuring of Soil Moisture

Figure 18:
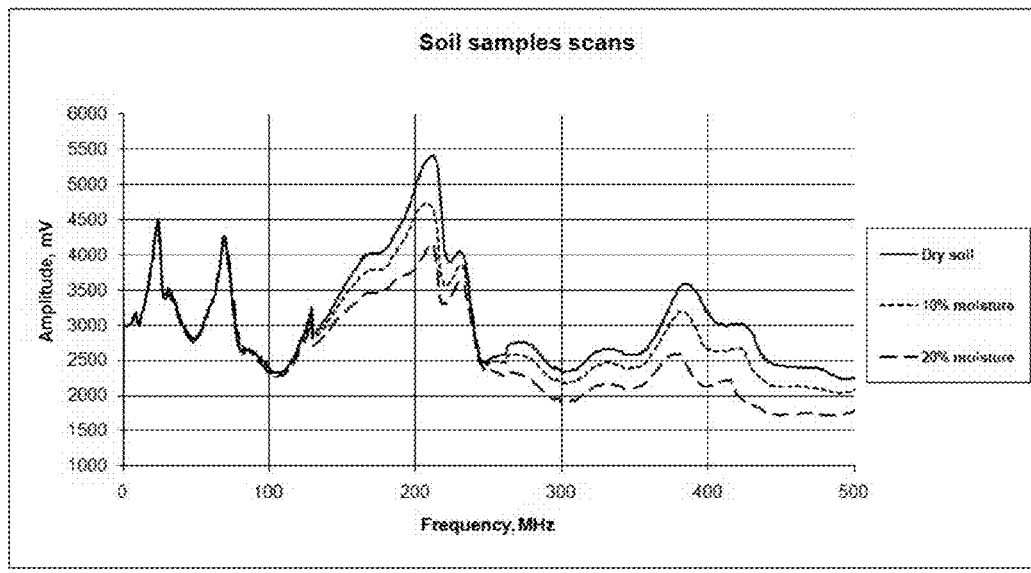
FIG. 18 depicts a graph of scans for soil samples with different percent of moisture made by using a potentiostate in accordance with one or more aspects of the present invention.

For identifying areas of electrical field frequencies where soil moisture gives good response, a potentiostate has been used. FIG. 18 shows a "screen shot" or graph of three soil samples with different moisture scanned with a potentiostate in a frequency range from 0 to 500 MHz. We can see on the screen shot/graph areas where graph plots for different soil samples split in amplitude. These are areas where phenomena of impedance spectroscopy take place. In those areas, influence of moisture may be defined. These scans show a large number of possible frequencies that could be used for measurement of soil moisture.

Figure 19:
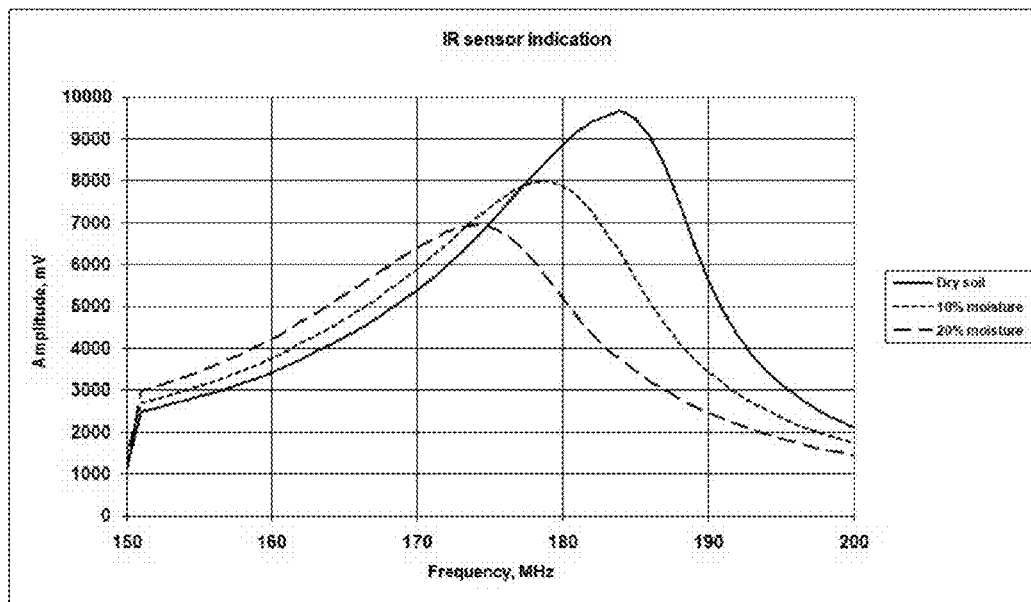
FIG. 19 depicts changing of an IR sensor's Gain-Frequency Variation when measuring soil samples with different percent of moisture in accordance with one or more aspects of the present invention.

Using data from the potentiostate we defined that at frequency from about 170 MHz to about 190 MHz we got sufficient sensitivity for measuring moisture. Those data permitted us to configure one or more IR sensor operating frequencies substantially close to those identified. Gain-frequency variations of the IR sensor are shown in FIG. 19. As it can be seen from FIG. 19, the changing of moisture from about 0% to about 20% causes a change of: (i) IR sensor resonant amplitude from ~about 9700 mV to about 7000 mV; and (ii) IR sensor resonant frequency from ~about 185 MHz to about 175 MHz. Thus sensitivity of the IR sensor is about 135 mV of resonant amplitude on one percent of soil moisture and about 5 MHz of resonant frequency on one percent of soil moisture.

2.5 Example 5

Use of an Impedance Resonance Sensor for Real Time Contactless Monitoring of Glucose in Saline One of the key components of intravenous solutions/drips (IVs) is saline, which is also known as, for example, the 0.9% sodium chloride (NaCl) solution. It is used frequently in IVs for patients who cannot take fluids orally and have developed or are in danger of developing dehydration or hypovolemia. Saline is typically the first fluid used when hypovolemia is severe enough to threaten the adequacy of blood circulation, and has long been believed to be the safest fluid to give quickly in large volumes. Also, saline solution could be used to deliver various drugs intravenously. Because Normal Saline is a close approximation to the osmolarity of NaCl in blood, we used it to conduct our experiments to verify if IR sensor technology could be used for identification of glucose concentration and, most importantly, to verify the possibility of using IR sensors for contactless identification of harmful levels of glucose in blood in real time.

Description of experiment:

1. We prepared saline solution by adding 9 g of NaCl to 1000 ml of distilled water.

2. In the saline solution was added glucose to make the following samples with glucose concentration of: 5000, 2000, 1000, 500, 250 and 125 mg/dL.

3. The samples were placed by turns in an IR sensor test fixture as shown in FIG. 11.

4. All measurements were conducted by sweeping frequency in a range from 96 to 100 MHz.

The below presented measurements from our experiments show quite promising results that give us a high degree of confidence that development of non-direct contact with a blood medical device to measure the level of glucose in the blood is possible when using IR sensor technology.

Figure 20:
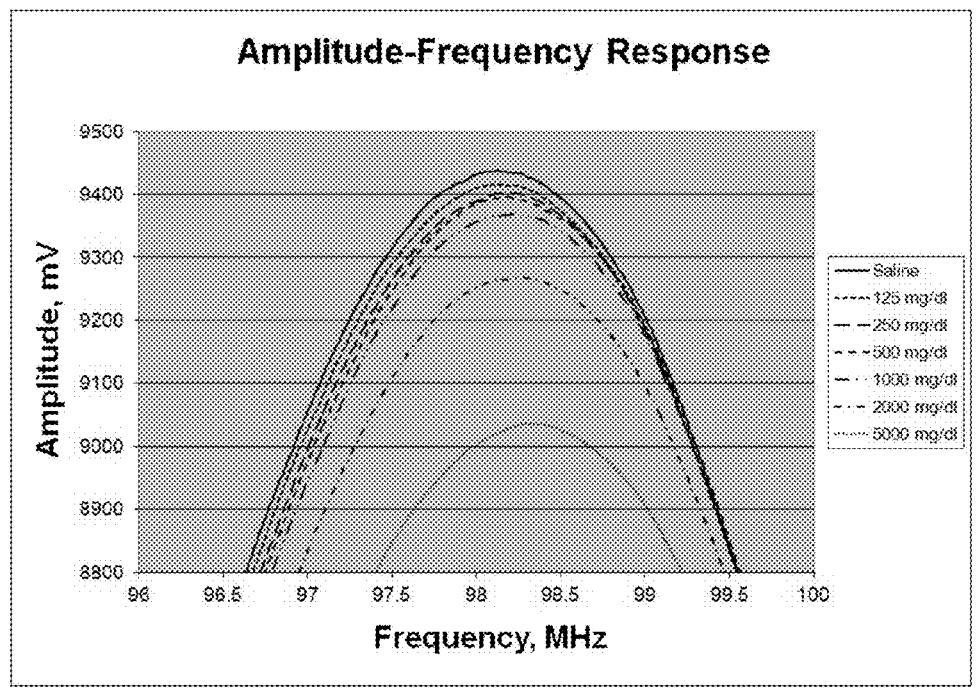
FIG. 20 depicts an IR sensor's Gain-Frequency Variations for different dextrose concentration in saline in accordance with one or more aspects of the present invention.
Figure 21:
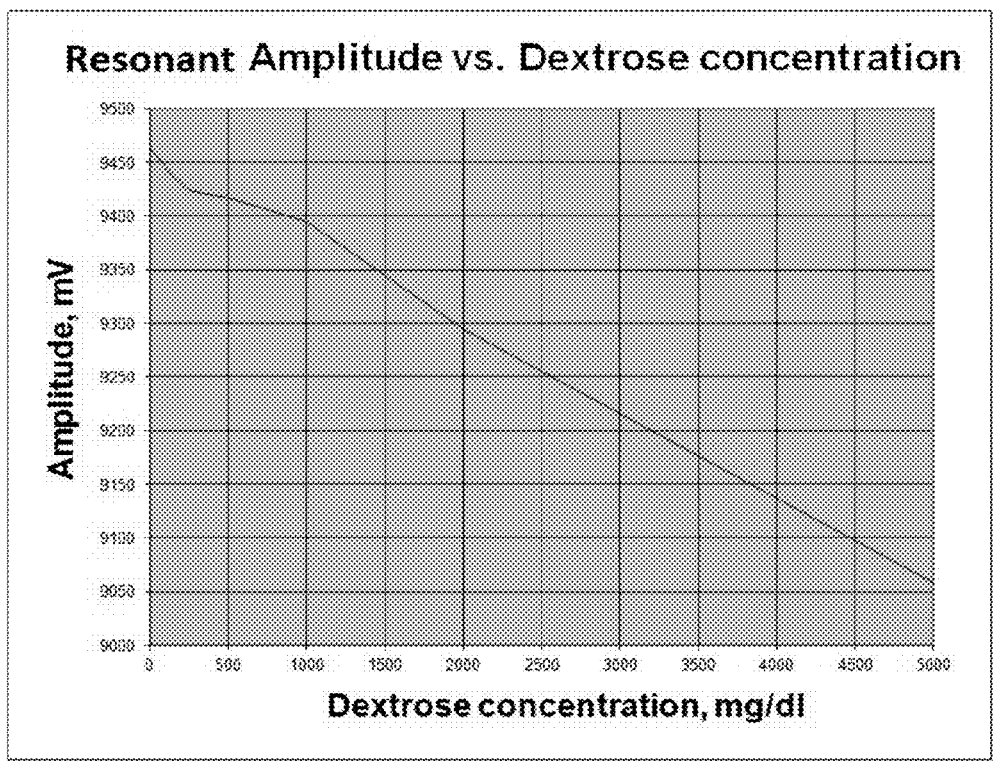
FIG. 21 depicts a graph of an IR resonance amplitude changing versus frequency for different dextrose concentration in saline in accordance with one or more aspects of the present invention.

Results of the measurement are shown in FIG. 20, FIG. 21, and Table 1.

TABLE 1

| # | Dextrose Concentration in Saline, mg/dl | IR-sensor's Resonant Amplitude, mV |
|---|---|---|
| 1 | 0 | 9462.97 |
| 2 | 125 | 9439.61 |
| 3 | 250 | 9423.82 |
| 4 | 500 | 9417.24 |
| 5 | 1000 | 9395.2 |
| 6 | 2000 | 9294.53 |
| 7 | 5000 | 9057.98 |

A monitoring device measures the concentration of glucose in a patient's tissue, blood, or other bodily fluids; provides an indication of the rate of change of such concentration; and determines whether the measured concentration and rate of change are within certain preset or predetermined limits. If not, an audible and/or visual alarm signal is generated. The patient monitoring system includes at least one IR sensor that is placed on the patient, where it produces sensor signals related to the concentration of the glucose in the blood that is being measured. The sensor's signals are displayed on the device's screen, or are delivered through a suitable interconnect cable to a monitor. The device interprets the sensor signals by applying a previously determined calibration to quantitatively determine the glucose concentration value. The glucose concentration value thus determined is then processed in order to determine the rate of change, is stored (to create a history or record), and may also be displayed in large, easy-to-read numerals. Rate of change information (trend) may also be numerically or graphically displayed.

As of today, we have conducted a number of experiments to identify frequencies at which we can distinguish different concentrations of glucose in the 0.9% sodium chloride solution that is also known as, for example, a Normal Saline ("NS")*. The output voltage of the IR sensor in relationship to the glucose concentration of 5000, 2000, 1000, 500, 250, and 125 mg/dl at a selected range of frequencies is presented in FIG. 20. Glucose concentrations were selected based on our understanding that the level of sugar of up to about 125 mg/dL is considered more or less normal and everything above that threshold will indicate various stages of diabetes, with anything above about 500 mg/dl indicating lethal levels.

All experiments were conducted with the sodium chloride 0.9% solution in order to eliminate the influence of any other liquid parameters and because most of intravenous glucose solutions are using similar concentrations of the sodium chloride (NaCl).

Normal saline—is the commonly-used term for a solution of 0.90% of NaCl, about 300 mOsm/L or 9.0 g per liter. NS is used frequently in intravenous drips (IVs) for patients who cannot take fluids orally and have developed or are in danger of developing dehydration or hypovolemia. As explained above, NS is typically the first fluid used when hypovolemia is severe enough to threaten the adequacy of blood circulation, and has long been believed to be the safest fluid to give quickly in large volumes. Because Normal Saline is a close approximation to the osmolarity of NaCl in blood we used it to conduct our experiments.

2.6 Example 6

Use of an Impedance Resonance Sensor for Real Time Contactless Measurements of Residual Chlorine in Tap Water In order to test effectiveness of the IR sensor for measuring residual chlorine in tap water we used a solution of POWER POWDER® PLUS containing Calcium Hypochlorite—73% as active ingredient (according to specification for that product which when mixed with water provides at least 70% Available Chlorine). To prevent contamination of water by residual chlorine in tap water, we used Alhambra® drinking water that we normally drink in our lab. For measuring residual chlorine concentration, we used SenSafe™ Free Chlorine Water Check Test Strips (USEPA Approved), which are sold by Industrial Test Systems, Inc., located in Rock Hill, S.C. (www.sensafe.com), with detection range: 0, 0.05, 0.1, 0.2, 0.4, 0.6, 0.8, 1.2, 1.5, 2, 2.6, 4, 6 ppm (mg/L). During our experiment, we used prior configured IR sensor. While various arrangements of the IR sensor's sensing element may be used, the IR sensor's sensing element used for this example is shown in FIG. 11. For laboratory experiments/measurements, it is convenient to use a sensor encompassing a vial, but for industrial in-situ measurements applications, the same sensor could encompass a pipe through which tap water or any other liquid will flow. Indeed, various types of vessels or tubes may be employed.

Figure 22:
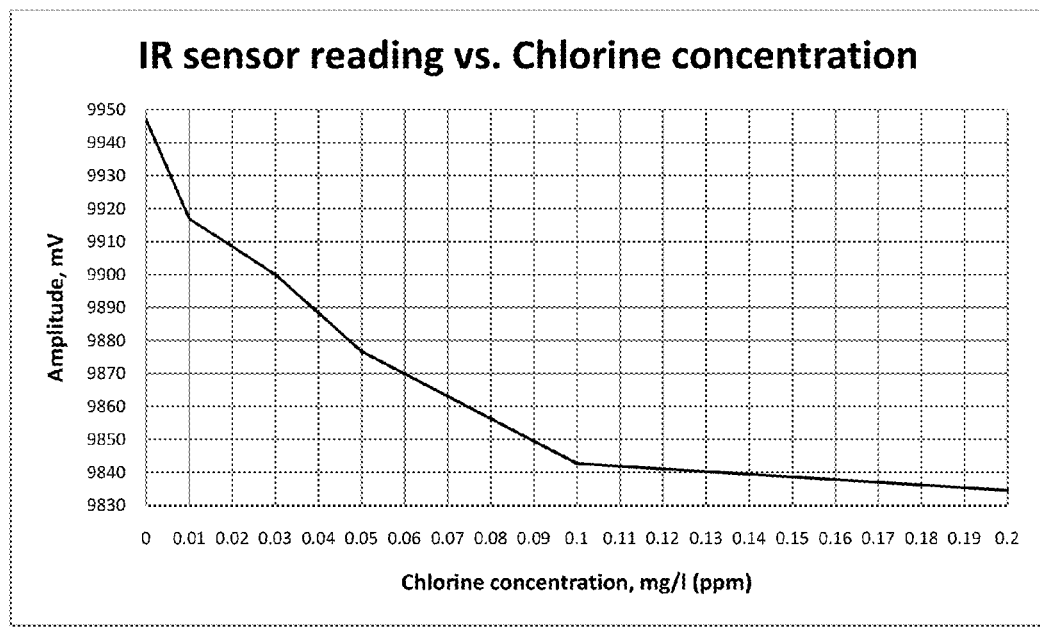
FIG. 22 depicts a graph of an IR resonance amplitude changing versus frequency for different residual chlorine concentration in Alhambra® drinking water in accordance with one or more aspects of the present invention.

Results of the measurements are represented in Table 2 and in FIG. 22.

TABLE 2

| # | Chlorine Concentration, ppm | IR-sensor's Resonant Amplitude, mV |
|---|---|---|
| 1 | 0 | 9946.88 |
| 2 | 0.01 | 9916.86 |
| 3 | 0.02 | 9908.5 |
| 4 | 0.03 | 9899.92 |
| 5 | 0.04 | 9888.31 |
| 6 | 0.05 | 9876.69 |
| 7 | 0.1 | 9842.68 |
| 8 | 0.2 | 9834.56 |

FIG. 22 shows that the IR sensor that we used for our experiments has very high sensitivity between 0.01 and 0.1 mg/L. The sensitivity of the sensor at high concentrations could be significantly increased by application of one or more additional or alternative configured specific sensing coil or coils.

At least one embodiment of the sensor that pertains to the present application is similar to one disclosed in our pending U.S. patent application Ser. No. 12/887,887, Filing Date: Sep. 22, 2010, the entirety of which is incorporated herein by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. An apparatus for contactless measuring or monitoring, in-situ, in-line and/or in real time, composition and/or other electromagnetic impedance correlated properties comprising at least one of level, density, moisture, and ionization of one or more liquid and/or gaseous substances and/or one or more bulk materials, comprising:

at least one resonance type impedance ("IR") sensor which is a multicoil open-core or air-core inductor, said sensor comprising at least two coils, at least one coil of the at least two coils being at least one excitation coil connectable to at least one alternating current source with frequency sweep and to at least one data processing system, at least one other coil of the at least two coils being at least one sensing coil, wherein:

(i) upon being connected to said current source, said at least one excitation coil is capable of propagating an energy to said at least one sensing coil, which is capable of generating a probing electromagnetic field, (ii) said at least one sensing coil is designed in such a way that intrinsic inductance L, capacitance C, and resistance R parameters of said at least one sensing coil are capable of providing resonance conditions for measuring impedance of an object under test or at least a portion of said object under test being disposed within a sensing area of said at least one sensing coil at a predetermined frequency range; and (iii) said at least one sensing coil uses only its intrinsic (distributed) capacitance and is not connected to any capacitance means such that said at least one sensing coil is capable of measuring at least one of conductance, conductivity and one or more dielectric properties of said object under test or at least said portion of said object under test being disposed within the sensing area of said at least one sensing coil;

at least one power supply;

at least one radio frequency ("RF") sweep generator for supplying said at least one excitation coil with alternating current;

at least one data acquisition block configured to measure either current through or voltage across said at least one excitation coil;

at least one calculation block; and at least one communication block.

2. The apparatus of claim 1, wherein said least one data acquisition block has high electrical input impedance.

3. The apparatus of claim 2, wherein said least one data acquisition block has electrical input impedance greater than 10 MΩ or substantially greater than 10 MΩ.

4. The apparatus of claim 1, wherein said object under test is capable of being at least one of conductive, semi-conductive and non-conductive.

5. The apparatus of claim 1, wherein said at least one data acquisition block registers a change of electric current through said at least one excitation coil.

6. The apparatus of claim 1, wherein said at least one data acquisition block registers a change of voltage across said at least one excitation coil.

7. The apparatus of claim 1, wherein said at least one data acquisition block registers a change of both current and voltage across said at least one excitation coil.

8. The apparatus of claim 1, wherein at least one data acquisition unit of said at least one data acquisition block registers a change of electric current through an excitation circuit and at least one other data acquisition unit of said at least one data acquisition block registers a change of voltage across said at least one excitation coil, the excitation circuit comprising said at least one radio frequency ("RF") sweep generator, said at least one excitation coil, and at least one instrument shunt resistor, wherein said at least one data acquisition unit registers a change of electric current by measuring a drop of potential on said shunt resistor.

9. The apparatus of claim 1, wherein said at least one sensing coil is immersible in, or is placed near or adjacent to, said object under test and/or a vessel or container having said object under test therein in order to benefit from at least one change of a distributed capacitance, and/or turn-to-turn capacitance, of said at least one sensing coil.

10. The apparatus of claim 9, wherein said at least one immersible sensing coil is coated with dielectric film to avoid any direct contact with at least one of liquid, gas and bulk material.

11. The apparatus of claim 9, wherein said at least one sensing coil and said at least one excitation coil are electromagnetically coupled with each other and are immersible in, or are placed near or adjacent to, said object under test and/or a vessel or container having said object under test therein.

12. The apparatus of claim 11, wherein at least one of said at least one immersible sensing coil and said at least one immersible excitation coil is coated with dielectric film to avoid any direct contact with at least one of liquid, gas and bulk material.

13. The apparatus of claim 9, wherein said at least one sensing coil is located inside of a vessel or pipe and immersed into said object under test, and said at least one excitation coil, which is electromagnetically coupled with said at least one sensing coil, encompasses said vessel or pipe.

14. The apparatus of claim 13, wherein said at least one immersible sensing coil is coated with dielectric film to avoid any direct contact with liquid, gas, or bulk material.

15. The apparatus of claim 1, wherein said at least one IR sensor is designed to measure and/or monitor at least one of:
 (i) one or more liquids and/or one or more gaseous solutions including at least one of:
  any lubricating product(s) used in operation of at least one of: any combustion engine, turbine and/or wind mill, and one or more electrical pumps in order to detect deterioration of one or more predetermined oil/fuel parameters including at least one of: soot content, metal particle(s), and change of viscosity;
  any fuel(s) and/or cooling substance(s);
  any gaseous substance(s) used to control any production process including heating, cooling, deposition or removal of films in semiconductor fabrication processes;
  any liquid and/or gaseous substance(s) used to control one or more medical and/or laboratory procedures and/or tests
  any liquid and/or gaseous substance(s) used to control at least one of: (a) one or more manufacturing processes for one or more pharmaceuticals, drugs and/or medicines; and (b) one or more testing and/or final testing of said one or more pharmaceuticals, drugs and/or medicines; and
  any type of drinking or process water;
 (ii) one or more quality metrics of slurry during a chemical mechanical planarization (CMP) process in order to replace or adjust a liquid mixture chemical composition to be in conformance with an industrial process based upon one or more detected changes in a tested liquid mixture, the one or more quality metrics including at least one of: (a) monitoring one or more abrasive properties of the slurry, (b) detecting particle size distribution (PSD), (c) large particle counts (LPC), (d) an oxidizer concentration, and (e) density; and
 (iii) one or more quality metrics of any industrial liquid chemical composition in order to replace or adjust a liquid mixture chemical composition to be in conformance with an industrial process based upon one or more detected changes in a tested liquid mixture.

16. The apparatus of claim 1, wherein said IR sensor(s) is(are) designed to measure and/or monitor moisture and analyte concentration of one or more bulk materials, the one or more bulk materials including at least one of:
 one or more agricultural bulk material products;
 one or more chemical bulk material products;
 one or more soils; and
 one or more building bulk materials.

17. The apparatus of claim 14, wherein at least one of:
 (i) the one or more agricultural bulk material products include at least one of one or more seeds, sugar, and flour;
 (ii) the one or more chemical bulk material products include at least one of one or more salts, one or more fertilizers, and one or more pesticides;
 (iii) the one or more soils include at least one of one or more sands and one or more clays; and
 (iv) the one or more building bulk materials include at least one of one or more sands and cement.

18. A method of measuring and/or monitoring conductive, semiconductive or non-conductive objects under test using the apparatus of claim 1, the method comprising:
 (A) measuring, at the same time, either: (i) self-resonance frequency and amplitude of said sensor(s); or (ii) amplitude and phase shift at a fixed frequency;
 (B) placing an object under test comprising at least one analyte or having at least one target or predetermined property;
 (C) measuring, at the same time, either: (i) resonant frequency and amplitude of said sensor(s) in the presence of said object under test; or (ii) amplitude and phase shift at a fixed frequency in the presence of said object under test;
 (D) calculating one or more changes in amplitude and resonant frequency induced by electromagnetic interaction between said sensor and said object under test to determine impedance of said object under test; and
 (E) matching said impedance with predetermined calibration data to determine one or more chemical or physical properties or said target or predetermined property of said object under test.

19. The method of claim 18, wherein said predetermined calibration data are prepared using one or more etalon samples.

* * * * *